United States Patent [19]

van der Jagt

[11] Patent Number: Plant 6,143

[45] Date of Patent: Apr. 5, 1988

[54] CHRYSANTHEMUM NAMED "RENINE"

[75] Inventor: Martinus van der Jagt, Ter Aar, Netherlands

[73] Assignee: Chrysanthemum Breeders Association, N.V., Curacao, Netherlands Antilles

[21] Appl. No.: 781,992

[22] Filed: Sep. 30, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

The present invention is a new and distinct variety of Chrysanthemum of a red bloom.

3 Drawing Sheets

BACKGROUND OF THE INVENTION

The present invention comprises a new and distinct cultivar of Chrysanthemum plant which is a cross of unknown parents. The invention was discovered by Martinus van der Jagt in June 1979 at Parad sweg 88, Ter Aar, Holland. The invention has been asexually reproduced by cuttings at the same location. The new cultivar has been found to retain its distinctive characteristics through successive propagations.

BRIEF DESCRIPTION OF THE DRAWINGS

The present invention of a new and distinct variety of Chrysanthemum is shown in the accompanying drawings, the color being as nearly true as possible with color photographs of this type.

FIG. 1 shows the full bloom of the new cultivar.

FIG. 2 shows various stages of bloom of the new cultivar.

FIG. 3 shows the foliage and stem of the new cultivar.

DESCRIPTION OF THE INVENTION

This new variety of Chrysanthemum is of the botanical classification *Chrysanthemum morifolium*. When grown in the vicinity of, Ter Aar, Holland, it has a response time of approximately 9 weeks. This new variety produces medium sized blooms having a 3 week performance.

This new variety of Chrysanthemum has been found to retain its distinctive characteristics throughout successive propagations and may be grown under greenhouse conditions between weeks 1 and 52.

The following is a description of the plant and characteristics that distinguish it over related variety and its antecedents:

Bud:
- *Size.*—Medium.
- *Form.*—Flat top.
- *Color.*—Near spiraea red 025/1.

Botanical classification: *Chrysanthemum morifolium.*

Bloom:
- *Size.*—Medium.
- *Fully open.*—7–8 cms.
- *Borne.*—Single.
- *Stems.*—Strong.
- *Form.*—Single.

- *Permanence.*—3 weeks.

Color:
- *Center of flower.*—Near spiraea red 025/1.
- *Base of petals.*—Near spiraea red 025/1.
- *Inside of petals.*—Near spiraea red 025/1.
- *Reverse of petals.*—Near spiraea red 025/1.
- *Outer petals.*—Near spiraea red 025/1.
- *Tonality from a distance.*—Red single with a green-yellow center.
- *Discoloration.*—To a pale purple upon maturity.

Petals:
- *Number.*—32–35 in two well-filled rows.
- *Arrangement.*—Imbricated.
- *Persistence.*—Good, less reflexion.
- *Fragrance.*—Chrysanthemum.

Reproductive organs:
- *Stamens.*—Normal.
- *Pollen.*—Normal.
- *Styles.*—Funnel-shaped and long, thick.
- *Stigmas.*—Big, yellow.
- *Ovaries.*—Enclosed in calyx.

Plant:
- *Form.*—Herbaceous.
- *Growth.*—Vigorous.
- *Height.*—Tall.
- *Peduncle.*—Normal.

Foliage:
- *Color.*—Dark green.
- *Size.*—Medium.
- *Quantity.*—Normal.
- *Shape.*13 Pointed.
- *Texture.*—Leathery.
- *Ribs and veins.*—Ordinary.
- *Edge.*—Deeply undulated.
- *Leaf underside.*—Very rough.
- *Leaf upperside.*—Smooth.

In the description above color references are made to the Horticultural Colour Chart I & II issued by the British Colour Council in collaboration with The Royal Horticultural Society, Copyright Robert F. Wilson, Vol I, 1938; Vol II, 1941, printed by Henry Stone and Son, LTD, Banbury, England.

I claim:

1. A new and distinctive variety of Chrysanthemum named "Renine" as described and illustrated in the foregoing specification and accompanying drawings.

* * * * *

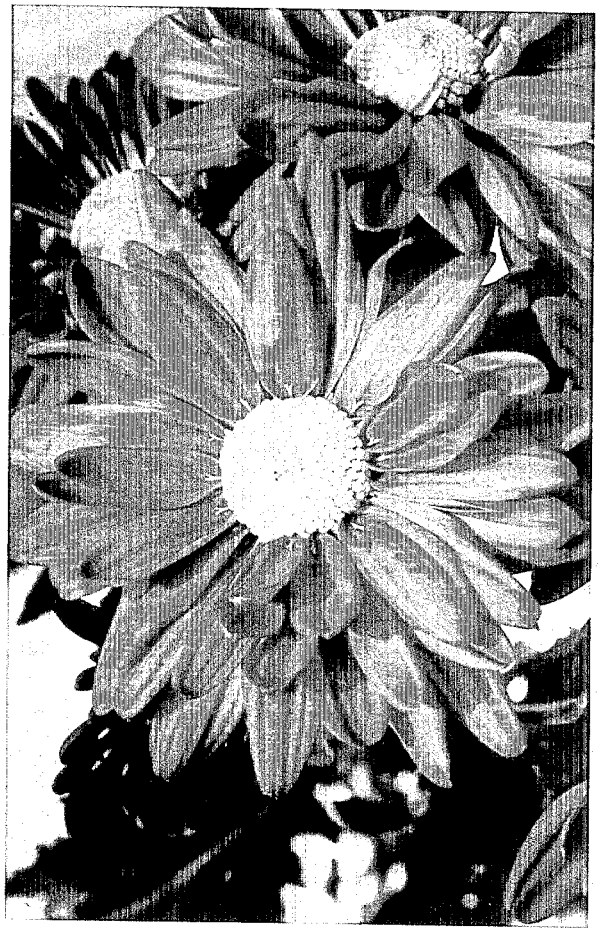

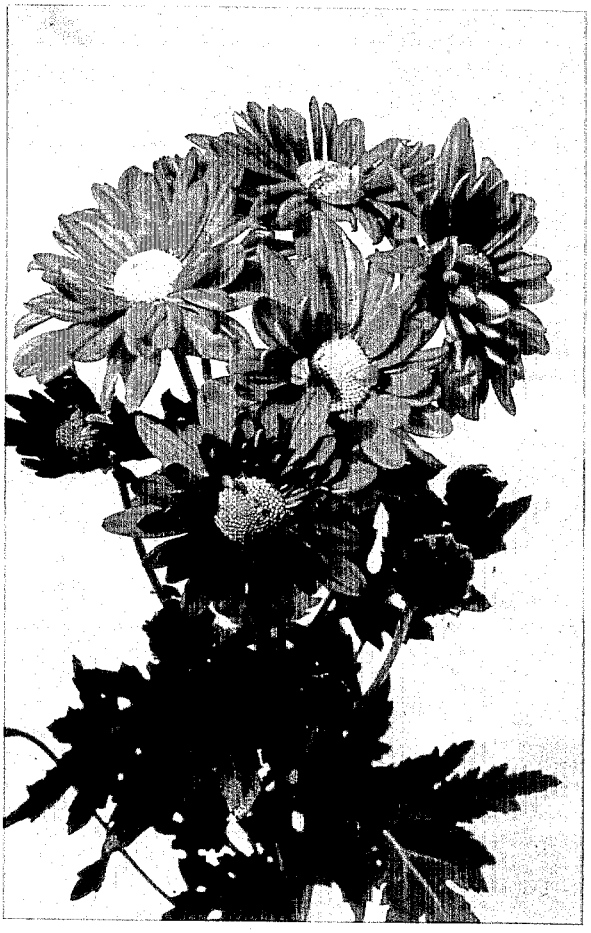

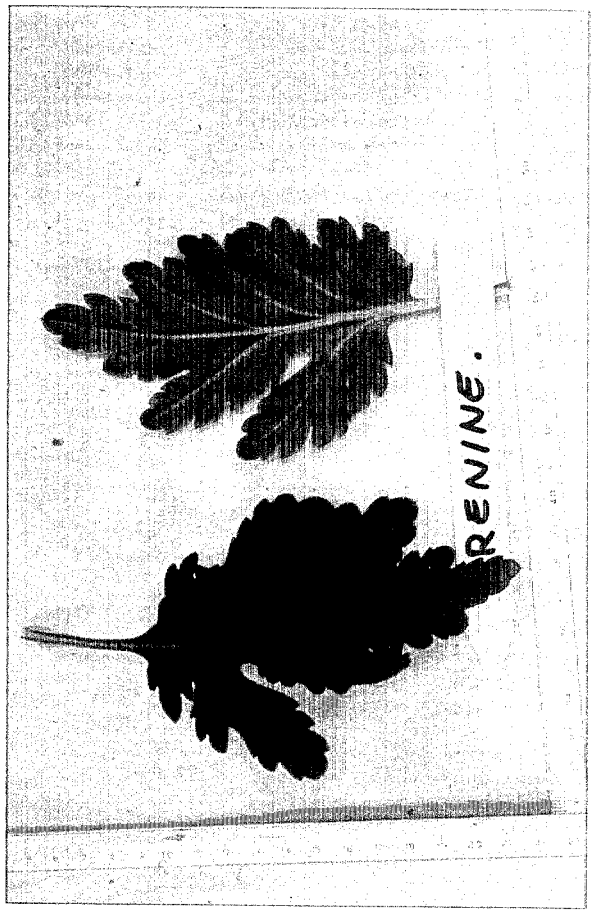
RENINE.